United States Patent

Leksell et al.

[11] Patent Number: 5,805,661
[45] Date of Patent: Sep. 8, 1998

[54] POSITIONING DEVICE AND METHOD FOR RADIATION TREATMENT

[75] Inventors: Dan Leksell, Stockholm; Börje Nilsson, Upsala, both of Sweden

[73] Assignee: Elekta Instrument AB, Sweden

[21] Appl. No.: 780,201

[22] Filed: Jan. 8, 1997

Related U.S. Application Data

[62] Division of Ser. No. 596,870, Feb. 13, 1996, Pat. No. 5,629,967, which is a division of Ser. No. 255,667, Jun. 9, 1994, Pat. No. 5,528,651.

[51] Int. Cl.⁶ .................................................. A61N 5/16
[52] U.S. Cl. ............................ 378/65; 378/68; 378/69
[58] Field of Search .................................. 378/34, 64, 68, 378/65, 69, 208; 256/492.1, 492.2, 492.22, 492.23, 492.3

[56] References Cited

U.S. PATENT DOCUMENTS

| | | | |
|---|---|---|---|
| 4,780,898 | 10/1988 | Sundqvist | 378/65 |
| 5,073,912 | 12/1991 | Kobayashi et al. | 378/34 |
| 5,168,512 | 12/1992 | Iwamoto et al. | 378/34 |
| 5,189,687 | 2/1993 | Bova et al. | 378/65 |
| 5,329,567 | 7/1994 | Ikebe | 378/65 X |
| 5,343,424 | 8/1994 | Stickel et al. | 250/492.23 |
| 5,369,679 | 11/1994 | Sliski et al. | 378/65 |
| 5,511,103 | 4/1996 | Hasegawa | 250/492.3 X |
| 5,528,651 | 6/1996 | Leksell et al. | 378/65 |
| 5,629,967 | 5/1997 | Leksell et al. | 378/65 |

*Primary Examiner*—David P. Porta
*Attorney, Agent, or Firm*—Theresa M. Gillis; Blaney Harper

[57] ABSTRACT

A radiotherapy appliance having a plurality of controllable radiation beams which converge on a focus volume wherein an object being irradiated can be movably positioned relative to the focus volume for varying time periods and with varying radiation exposure rates, optimally under control of a computer. The computer controls the focus volume radiation beam size, intensity, and exposure time for subareas of the treatment target in response to a radiation dose distribution determined for the treatment target. A determination of the radiation beam size, intensity, and dwell time of the focus volume in the target area, is made by initially dividing up the specified treatment area into volume elements or voxels and having biological characteristics of the treatment area assigned to each voxel. The energy deposition incident to each voxel to provide this biological characteristic is then calculated. Finally, from the energy deposition incident on each voxel, the dwell time of the focus volume at particular voxels can be determined. Once the dwell time has been determined, the computer generates a sequence of motor control movements to move the patient with respect to the focus volume such that the focus volume is at a position sufficiently long within the treatment target to deliver the necessary radiation for each voxel.

7 Claims, 5 Drawing Sheets

POSITIONING DEVICE AND METHOD FOR RADIATION TREATMENT

This application is a divisional application of Ser. No. 08/596,870, filed Feb. 13, 1996, now U.S. Pat. No. 5,629,967, which is a divisional application of Ser. No. 08/255,667, filed Jun. 9, 1994, now U.S. Pat. No. 5,528,651.

FIELD OF THE INVENTION

This invention relates to a method and device for treating a patient with ionizing radiation. In the practice of the invention, a patient is moved relative to an ionizing radiation source during treatment. By moving the patient during treatment, it is possible both to minimize radiation delivered to areas outside a target volume and to take into consideration, in treatment planning, the biological properties of different areas inside and outside the target volume.

BACKGROUND OF THE INVENTION

It is known that exposure of tissue to ionizing radiation will kill the cells exposed. In the process of conventional radiation therapy, however, significant volumes of normal tissue in addition to pathological tissue, are exposed to harmful levels of radiation.

Several methods have been employed in the prior art to minimize the exposure of healthy tissue to ionizing radiation. For example, devices which direct radiation at the tumor from a number of directions have been used. In such devices, the amount of ionizing radiation emanating from each source of radiation is less than that which is necessary to destroy tissue. Rather, tissue destruction occurs where the radiation beams from multiple sources converge, causing the radiation level to reach tissue-destructive levels. The point of convergence of the center of multiple radiation beams is referred to herein as the "focus point." The radiation field surrounding a focus point is herein referred to as the "focus volume." The size of the focus volume can be varied by varying the size of the intersecting beams.

One such radiation appliance sold under the name GAMMA KNIFE (Elekta Instruments S.A.) comprises an ionizing radiation shield having a substantial number of ionizing radiation sources. Radiation passes through a number of channels all of which lead toward a common focus point in a recess within the radiation shield. Such a system is referred to, and described in, U.S. Pat. No. 4,780,898. Another system commonly termed a LINAC (or linear accelerator) involves an ionizing radiation source which moves circumferentially around a focus point delivering a series of beams of ionizing radiation through the focus volume. A patient's head, immobilized in a stereotactic instrument which defines the location of the treatment target in the patient's head, is secured by a system which positions the treatment target in coincidence with the above-mentioned focus point.

The ionizing radiation in the focus volume of these radiation appliances is intense compared to the radiation emanating from each individual beam of the device. Areas outside of the focus volume receive less substantial amounts of ionizing radiation. Therefore, pathological tissue can be treated while avoiding surrounding healthy areas.

In general, the focus volume is spherical because the intersection of multiple radiation beam cross sections approximately form a sphere of constant radiation density at each point equidistant from the focus point. As a result, when the shape of the pathological tissue volume is not substantially spherical, either some areas of pathological tissue do not receive enough radiation or other areas of healthy tissue receive too much radiation. In other words, variations in radiation sensitivity within the focus volume cannot be taken into account. To ensure that the whole volume of pathological tissue is fully exposed to the radiation field, the radiation team is obliged to deliver damaging doses of radiation to healthy tissue within the focus volume.

It is possible to reduce the volume of healthy tissue receiving high ionizing radiation doses by reducing the size of the focus volume and manually repositioning the patient a number of times such that the different positions of the various focus volumes would effectively cover the entire pathological tissue volume. While this method allows increased conformity between pathological tissue volume and shape and the volume receiving high radiation doses, the time required to manually reposition a patient a sufficient number of times for the selected focus volume size to effectively cover the pathological tissue can require unreasonably long treatment periods. Moreover, each manual reposition introduces the potential for mistakes with resultant increased radiation of healthy tissue.

A second potential means for minimizing the irradiation of healthy tissue would be to vary individual beam sizes and intensities whereby the shape of the focus volume could be modified to conform more accurately with the pathological tissue volume. With the many possible combinations of incident beam sizes and intensities to be interactively evaluated by the radiology team in order to find a radiation dose distribution appropriate for treating a pathological tissue volume having a specific shape, the experience of the radiotherapy team in choosing the beam sizes and intensities becomes a significant factor in the efficiency and effectiveness of the radiation treatment.

A further solution involves the projection of a focus volume of ionizing radiation onto a treatment area. Such a technique is described in, for example, *Experimental Verification of an Algorithm for Inverse Radiation Therapy Planning*, Radiotherapy and Oncology, 17 (1990) 359–368. According to this article, it is impractical to move the patient with respect to a fixed focus point. This conclusion was based on *Therapy Planning and Dosimetry for the Pion Applicator at the Swiss Institute for Nuclear Research*, Radiation and Environmental Biophysics, 16, 205–209 (1979), which was reported to have demonstrated that dynamic movement of the patient in a pion generator was not feasible.

Thus, although the prior art suggests radiation treatment of an object in which the dose distribution closely conforms to the treatment area within the object, the methods are dependent on the skill and experience of the radiology team, involve potential errors during manual repositioning require prolonged treatment times. In contrast to these prior art methods, the present invention—by means of automatic positioning and repositioning of a target area relative to a focus volume—eliminates the risks of manual error, allows use of smaller focus volumes, thereby improving conformity between a radiation field and a target volume and reducing the need for trial and error approach associated with multiple size focus volumes, and shortens the treatment planning time. In addition, contrary to the teaching of the prior art, the present invention permits dynamic movement of an object relative to a radiation source, whereby greater local conformity of dose delivery to pathological tissue volume and shape becomes possible by movement at rates which modulate radiation deposition based on the tissue cellular properties such as radiation sensitivity both inside and outside of the target volume.

SUMMARY OF THE INVENTION

The present invention provides a medical radiation treatment method and apparatus having a focus volume, the position of which remains fixed with respect to the ionizing radiation source but is variable with respect to the object to be radiated. In the practice of the invention, an object is moved with respect to the focus volume of an ionizing radiation source whereby a plurality of subareas within the object are subjected to varying radiation intensity levels for varying dwell times. The dynamic movement is guided by a computer controlled positioning device to provide a radiation dose distribution. The radiation dose distribution closely conforms to a desired radiation dose distribution taking into account both the biological response of the various tissues being subjected to radiation and the shape of the target volume. The focus volume size and shape may be varied in cooperation with the movement of the object to further optimize the radiation treatment.

A determination of the focus volume size, intensity, and dwell time of the focus volume in the target area, is made by initially dividing up the specified treatment volume into volume elements or voxels. Biological characteristics of the treatment volume are then assigned to each voxel. A probability for achieving complication free control of pathological tissue is then calculated for each voxel based on the biological characteristics. The energy deposition incident to each voxel which is needed to provide this probability of complication free tumor control is thereupon calculated. Finally, from the energy deposition incident on each voxel, the dwell time of the focus volume at particular voxels is determined. Once the dwell time has been determined, it is possible to determine the order of movements necessary to position the object with respect to the focus volume to deliver the necessary radiation for each voxel.

A device which allows a patient to be dynamically positioned with respect to the focus point is used to practice the method of this invention. In this device, a computer is used to generate a number and order of motor control movements which cause the target volume to be moved and positioned with respect to the focus point for the requisite time. In a preferred embodiment, a positioning device is attached to a suspension arrangement which is secured to a radiation appliance and is translatable in the X, Y and Z directions via two electronically controlled motor assemblies.

DETAILED DESCRIPTION OF THE INVENTION

Figure 1:
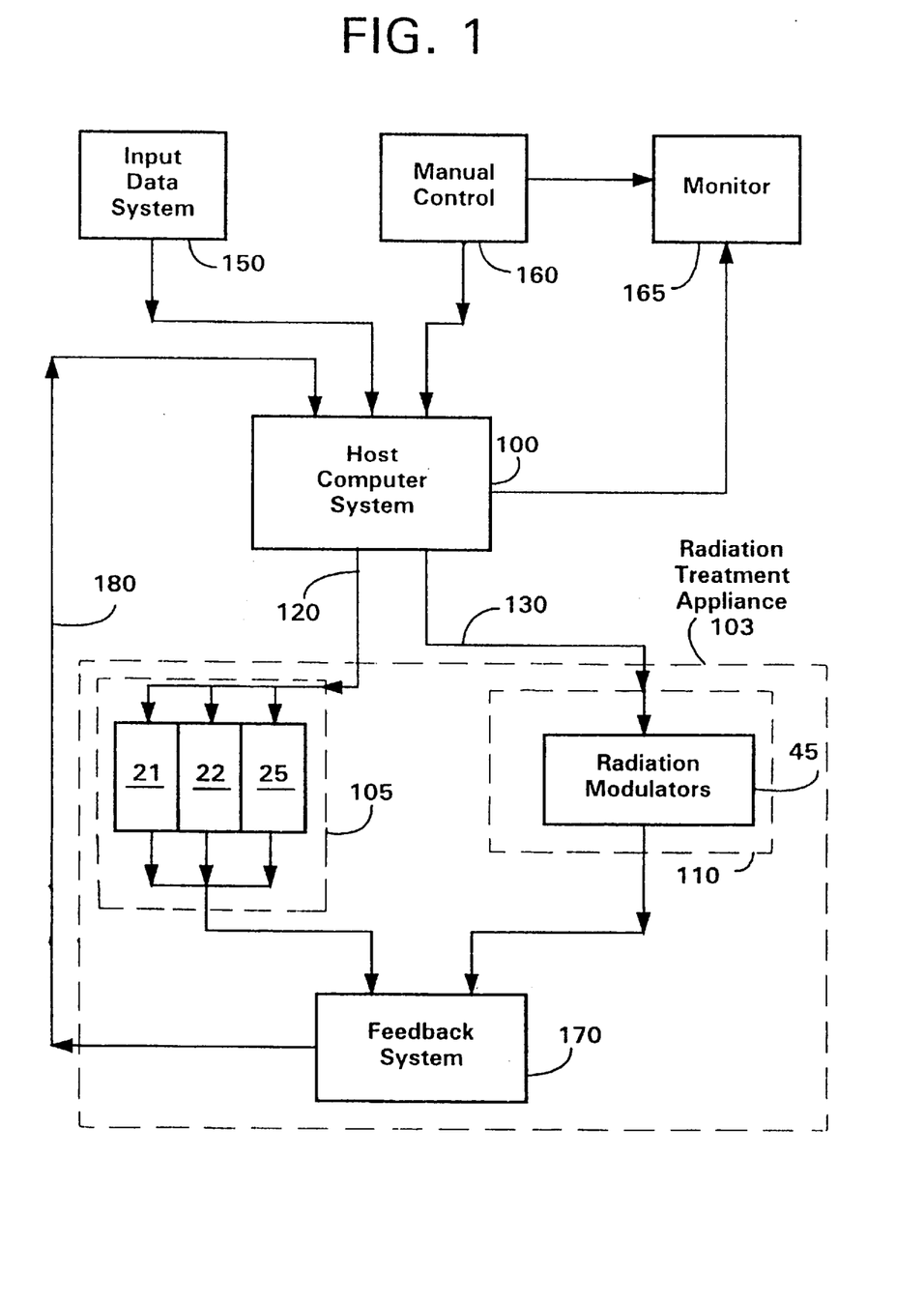
FIG. 1 illustrates a radiation treatment system according to the present invention.

FIG. 1 illustrates a radiation treatment system useful for carrying out the radiation treatment method according to the present invention. In particular, FIG. 1 illustrates the coordination of various parts of a radiation treatment appliance 103, having an electronically controlled positioning device 105 and an ionizing radiation unit 110, to deliver controlled radiation to selected parts of an object under treatment. The use of an electronically controlled positioning device in combination with calculated radiation doses for individual voxels based on biological radiation response characteristics enables the radiation system illustrated in FIG. 1 to dynamically control the radiation treatment of the target by moving the target with respect to the focus point. Specifically, the radiation treatment system of FIG. 1 optimizes the radiation delivery of individual voxels on a real time basis so that radiation absorbed in the target conforms to the desired radiation doses associated with desired biological responses of the various tissues to be treated.

Figure 2:
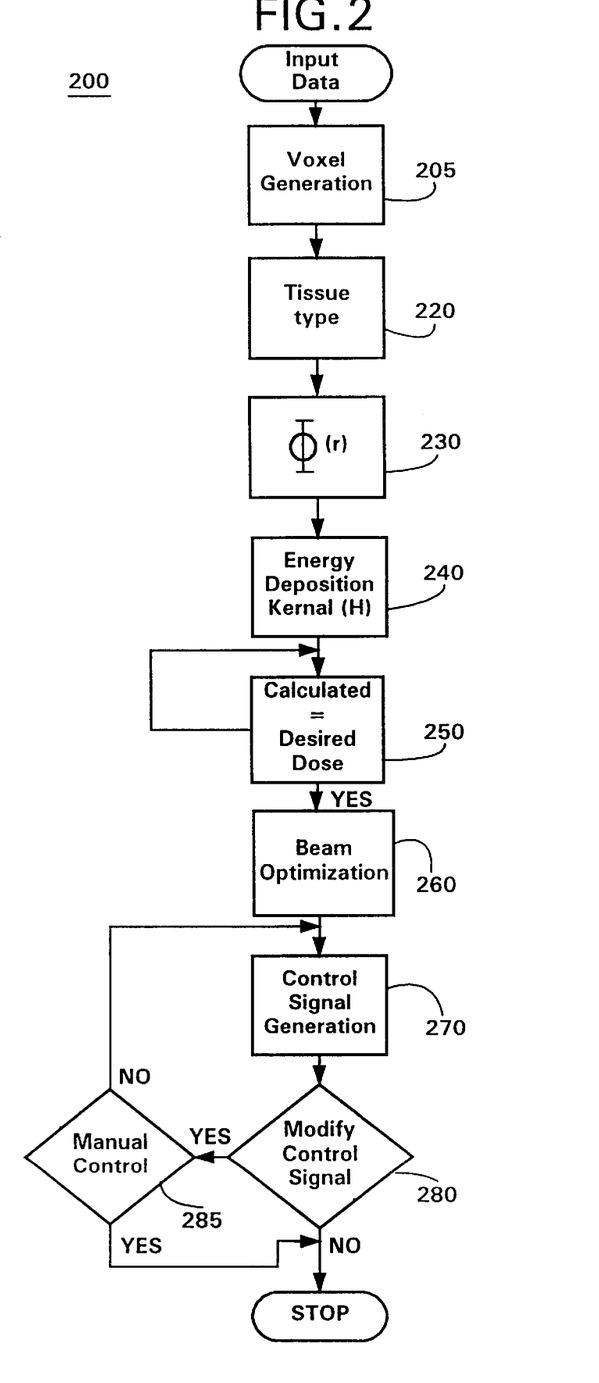
FIG. 2 illustrates a flow chart for a computer program for use in a radiation treatment system according to the present invention.

Input data system 150, illustrated in FIG. 1, comprises a system for generating and/or storing three dimensional geometric coordinates of the treatment volume within an object such as a patient. This system also generates and/or stores the types of biological responses of the target volume and surrounding tissues to be treated. The input data system 150 transmits the treatment volume data to the host computer system 100. The input data system 150 is, for example, a conventional computer graphics system which stores three dimensional coordinates of a treatment volume and associated subvolumes of the treatment volume with data representing biological properties of the subvolumes. The host computer 100 converts this data into a series of motor control, radiation beam size, and radiation beam energy output control signals through a computer program such as illustrated in FIG. 2. The host computer sends radiation control signals to the radiation modulators 45 of the radiation unit 110 device over channel 130 to control the size and/or intensity of the radiation beams emanating from the radiation source to irradiate the treatment volume.

The radiation unit lo includes an ionizing radiation source which projects one or more beams of radiation and a means to control radiation beam size, such as modulators 45. The radiation source of the radiation treatment appliance may be any of a variety of conventional ionizing radiation sources which produce an effective focus volume of radiation. A focus volume is typically formed by the intersection of a plurality (2 to several hundred) of radiation beams emanating from the radiation source. The beam axes are directed at a fixed point with respect to the radiation source. The focus volume is the summation (over the volume of the intersecting radiation beams) of radiation densities from each of the intersecting radiation beams. An effective focus volume can also be formed by directing the axis of a single radiation beam through a fixed point from a plurality (typically 2 to 360) of different angles. Such a technique is commonly used in linear accelerator type radiation units.

The host computer 100 also sends the motor control signals through channel 120 to each of a first and a second motor assemblies, each having motors 21, 22, and 25, within the electronically controlled positioning device 105. The first and second motor assemblies cooperate so that motors 21, 22 and 25 in the first assembly always move precisely the same distance as motors 21, 22 and 25 in the second assembly. The first and second motor assemblies are each connected to feedback system 170 which compares the translation distances of motors 21, 22, and 25 in the first motor assembly with the translation distances of motors 21, 22 and 25 respectively of the second motor assembly. When a pair of cooperating motors 21, 22, or 25 do not have approximately (i.e. >0.2 mm difference) the same translation distance, an error detection feedback system 170 generates a feedback error signal to terminate all motor movement and radiation exposure which is sent through channel 180 to the host computer system 100. When the computer system has terminated motor movement and radiation exposure due to this feedback signal, the motors can then be recalibrated, and treatment restarted. Feedback system 170 also monitors the radiation intensity by monitoring the beam sizes produced by the radiation modulators which form the focus volume. The beam size is controlled by the host computer 100 through radiation modulators 45 for each beam. When a modulator forms a beam having a cross section larger or smaller than desired, then the error detection feedback system 170 transmits an error signal to the host computer which, in turn, generates control signals to the cooperating motors which move the patient away from the focus volume of the radiation treatment appliance. Alternatively, when the error detection feedback system 170 senses that the radiation beam size is not correct, then feedback system 170 transmits an error signal to the host computer 100 which then turns off the radiation source.

Manual controller 160 consists of a joystick mechanism or the like which generates signals for manually controlling cooperating motors 21, 22, and 25. These signals are transmitted to both sets of cooperating motors 21, 22, and 25 over channel 120 through host computer system 100. Monitor 165 displays an image corresponding to a focus point and a treatment volume as the treatment volume is moved with respect to the focus point in response to the signals sent to cooperating motors 21, 22, and 25.

FIG. 2 illustrates a computer program 200 used by a computer 100 of the radiation treatment system according to the present invention for controlling radiation deposition within the treatment volume of an object by automatically moving the object with respect to the focus volume. The computer program generates signals to control motors which move the object so as to have a radiation focus volume dwell in a location for a sufficient time to deliver the appropriate radiation intensity for that location. Initially, the three dimensional coordinates of the treatment volume and the biological characteristics of the tissue in the treatment (and surrounding) volume are generated and sent 203 to the computer system. The treatment volume is then segmented 205 into volume elements or voxels having a minimum volume smaller than the focus volume which is generated at the intersection of the radiation beams. Biological responses to radiation of tissue associated with the treatment area are then assigned 220 to the voxels. The specification of tissue types allows the treating physician to treat, through computer controlled radiation, different types of tumorous regions which may react differently to specific radiation doses.

Once the tissue types for each voxel have been established, the computer program 200 selects a desired biological response 230 for each voxel which depends on a radiation dose for that voxel. This selection generates a desired radiation dose distribution $\Phi(r)$ for the treatment volume. A specific example of such a biological response is the maximum probability of complication free control of pathological tissue (P+) chosen for each voxel. P+ is the probability of achieving control for a specific type of tissue for a specified radiation dose minus the probability of fatal complications for that radiation dose and tissue type. The data relating to the probability of control is provided to the computer program from ongoing or previously published clinical studies. Selecting a maximum P+ for each voxel generates an optimum radiation distribution for pathological tissue control because each selected P+ has an associated radiation dose. The generation of P+ can alternately be defined as the probability of control for a specific type of tissue for a specified radiation dose minus the probability of adverse (not necessarily fatal) complications from that radiation dose for that type of tissue. Alternatively, biological responses of tissue to radiation may be selected depending on the location of the treatment volume relative to other treatment volumes. Further, other biological responses of tissue to radiation may be chosen which would generate different radiation dose distributions for the tissue. These selections of biological responses provide a treating physician more degrees of freedom in treatment doses for different types and locations of tissues.

Once a desired radiation dose $\Phi(r)$ for each voxel has been generated in step 230, the computer program 200 must specify how any particular voxel will receive the required dose. This is a problem because radiation beams focused on any one voxel will contribute radiation exposure to adjacent voxels. The computer program 200 solves this problem by first determining 240 an energy deposition kernel $H(r,r')$ which is the mean specific energy imparted to a point r per unit energy incident on a volume centered at r'. The program 200 assumes that $H(r,r')$ is spatially independent. That is, the energy imparted at point r from a focus volume centered at r' is only a function of the distance between r and r'. A consequence of this assumption is that the calculated dose distribution $D(r)$ can be expressed as the integral of the density $F(r')$ of energy deposition kernels $H(r, r')$ over the same volume. The integral expression is then solved via conventional analytical or iterative techniques for one of $D(r)$ or $F(r')$ given $H(r, r')$ and either $F(r')$ or $D(r)$ respectively. The energy deposition kernels $H(r, r')$ are known and are inputs for the integral expression because the energy distribution associated with the physical intersection of multiple radiation beams of a given cross section for any one focus volume is known. The kernel may be simulated, for example, by rotating a normalized beam cross section through 360 degrees. Energy deposition kernels H are assigned to each voxel in step 240.

Once the energy deposition kernels for all voxels have been determined, the calculated radiation dose distribution $D(r)$ is determined by iteratively solving for the radiation density $F(r')$. That is, an initial density $F_0(r')$ for each voxel is assumed, multiplied by the deposition kernel for each voxel, and then summed over the total treatment volume. The initial calculated dose distribution $D_0(r)$ is then compared 250 to the desired radiation dose $\Phi(r)$ and an error term is generated. The assumed initial density is adjusted $F_1(r')$ as a function of the error term and the next $D_1(r)$ is calculated. This iteration procedure continues until the calculated $D_n(r)$ after n iterations is sufficiently close to the desired $\Phi(r)$. The initial assumed density is chosen to deliver a substantial overdose to the treatment area. The error term represents a decrease in beam density. As a result, the convergence of the iterative calculations will guarantee that the treatment area will not receive less than the desired dose. This consideration assures that there will not be an underexposure of a treatment area. The result or iteration step 250 is a density F(r) for each voxel which specifies the time duration that a specific kernel should dwell on any one voxel. Typically, the iteration converges at approximately n=200 or before.

Once the duration of a specific kernel on any particular voxel is known, the computer 100 generates (270) control signals which are sent to the modulators 45 and to both sets of cooperating motors 21, 22, and 25. The control signals sent to the modulators 45 adjust the radiation beam size, and hence the kernel size for any selected voxel. The control signals sent to the cooperating motors 21, 22, and 25 move the patient with respect to the focus volume such that the radiation energy incident on the focus volume has a duration on any particular voxel only long enough to deliver the required beam density to that particular voxel. The movement of the target volume relative to the focus volume may be continuous while the target volume is exposed to radiation and the speed may be slowed or accelerated to result in an appropriate dwell time. Alternatively, movement may comprise sequential movement or re-positioning of the target volume in a multiplicity of positions relative to the focus volume. In this case, the radiation source is pulsed off while the target volume is moved and pulsed on while the target volume is stationary. As used herein, the term "sequential movement" means the stopping the movement of the target volume, irradiating the target volume, and moving the target volume again. In a preferred embodiment, the focus point is not roved outside of the object containing the target volume while this sequential re-positioning is occurring.

Cooperating motors 21, 22, and 25, as well as modulators 45 will continue to control the radiation deposited in the patient until the feedback system 170 of the radiation treatment system detects that either the opposing motors are not moving synchronously or that one or more of the radiation sources are not producing the required beam intensity or that the modulators 45 are not producing the required beam shape. When either of these conditions occur, the computer program will generate 280 commands to stop motor movement and/or stop radiation exposure. At this point, the program 200 will prompt the user 285 for an evaluation of whether to proceed with the remaining computer controlled treatment or proceed with manual operation. When the user wants to return to computer control, a new sequence of control movements are generated 270 taking into account that part of the previous treatment already accomplished. When the user requests manual operation, the program releases control over the radiation treatment system and transmits signals from the manual controller 160 to both sets of cooperating motors 21, 22, and 25.

Figure 3:
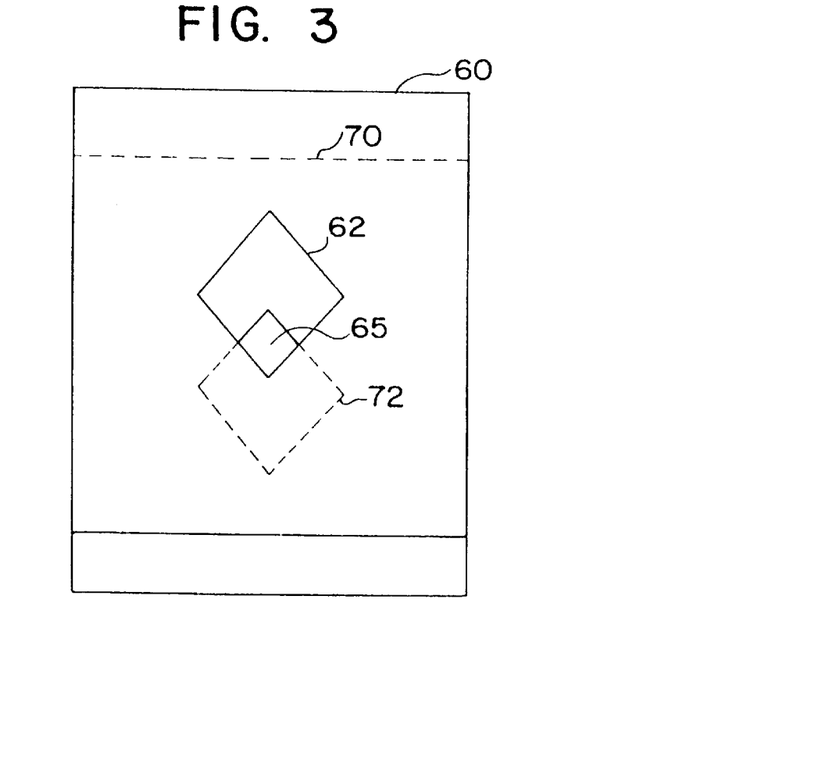
FIG. 3 illustrates a modulator suitable for use in a radiation treatment appliance according to the present invention.

The apparatus described above may be adapted to any radiation unit 110 which delivers ionizing radiation to a focus volume such as a Gamma Knife™ or LINAC radiation treatment system, or a heavy particle beam system. In order to control radiation delivery, the channel(s) through which radiation is delivered may be provided with radiation modulators 45 such as shown in FIG. 3. The radiation modulators 45 may be configured as opposingly faced lead plates or wedges or the like which are moveable relative to each other to form a variable slit or opening for modulating the shape or intensity of the radiation beam passing through the opening.

Figure 4:
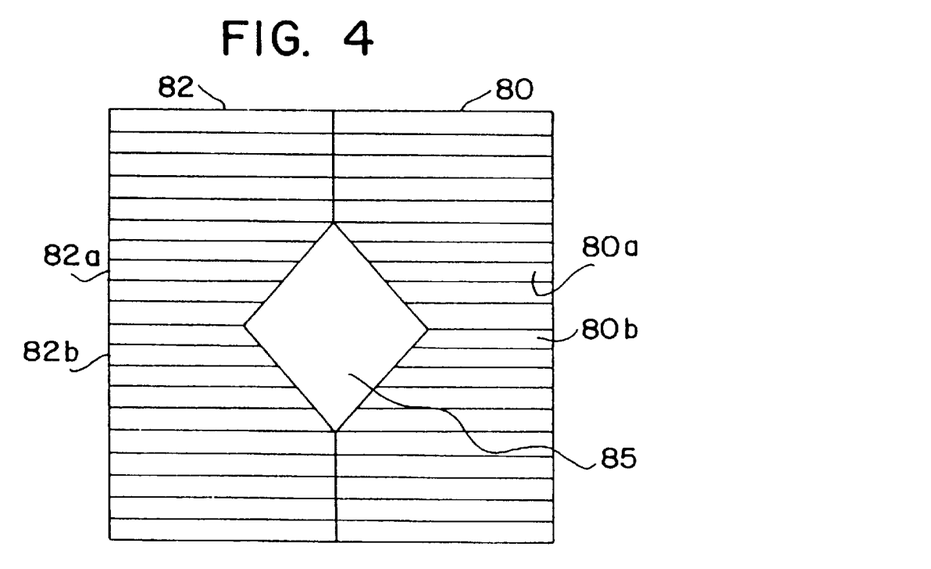
FIG. 4 illustrates an alternate form of modulator suitable for use in a radiation treatment appliance according to the present invention.

FIG. 3 illustrates a top view of modulator 45. In particular, moveable lead plate 60 is disposed over moveable lead plate 70. Plate 60 has a diamond shaped opening 62 therethrough and plate 70 has a diamond shaped opening 72 therethrough. Openings 62 and 72 converge to form opening 65 through both plates 60 and 70. The relative position of plates 60 and 70 determine the size of opening 65 through which a radiation beam passes. The size of opening 65 shapes the radiation beam passing through opening 65. FIG. 4 illustrates an alternate form of modulator suitable for incorporation in the present invention. The modulator illustrated in FIG. 4 is formed from two sets 80 and 82 of opposingly oriented slats of radiation blocking material. The slats may also be formed of radiation modulating material which transmits selective intensities of radiation depending on the energy of the incident radiation. Individual slats within a first or second set form a planar surface substantially perpendicular to the direction of the radiation beam. The two sets of slats are oriented with respect to each other such that they form the radiation beam cross section. The slats are moveable with respect to each other, and as they are moved, the beam cross section is modulated. For example, slat 80(*a*) moves relative to slat 82(*a*) to form part of opening 85 and slat 80(*b*) moves relative to slat 82(*b*) to form another part of opening 85. Any other suitably shaped and sized modulator may be used in the practice of the invention.

The radiation sources within the radiation unit 110 are preferably ionizing radiation sources which emit high energy (gamma or x-ray) photons or heavy charged particles.

Figure 5:
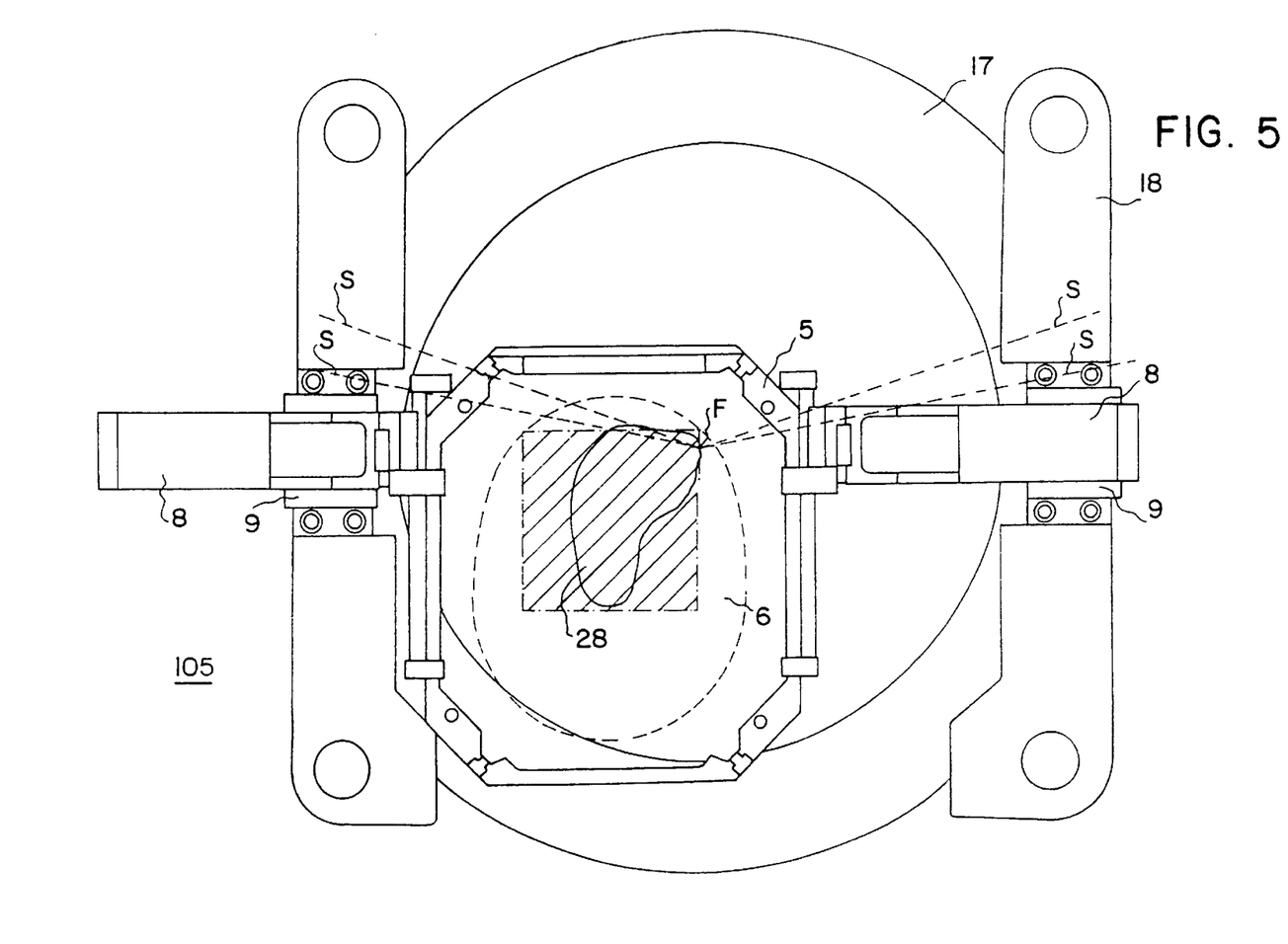
FIG. 5 illustrates a suspension system for moving a positioning device with respect to a radiation source according to the present invention.

As illustrated in FIG. 5, an object such as a patient's skull 6 is immobilized with respect to a fixation device 5 within an electronically controlled positioning device 105. The electronically controlled positioning device 105 includes a base 17, a suspension system, and a fixation device 5. The fixation device 5 is moveable with respect to the radiation device. During treatment, the frame 5 is moved by the positioning device to the positions necessary to allow the focus point F of the radiation beams to be located within the target volume 28. The focus point is at the intersection of the plurality of radiation beams S. The positioning device is secured to the radiation appliance by a base 17. The suspension system, attached to the base 17 by bracket 18, translates the fixation device 5 in the horizontal and vertical planes, i.e. the 3 dimensional coordinate system, with respect to the radiation source and the focus point F. This suspension arrangement comprises a pair of horizontal beams 8 or the like which are oriented in line with each other, translatable in their lengthwise direction, and slidably supported in associated guides 9 of bracket 13.

A fixation device 5 suitable for use in this invention when immobilizing a patient's skull in the positioning device is, for example, a stereotactic frame. The frame is fixed to the skull of the patient and mounted to the suspension system. The frame may be fixed to the skull of the patient by means of surgical twist drills passing through skin and locking into underlying bone. Alternatively, the fixation device 5 may be one which is non-invasive and/or allows the frame to be relocatably positioned on the patient.

Figure 6:
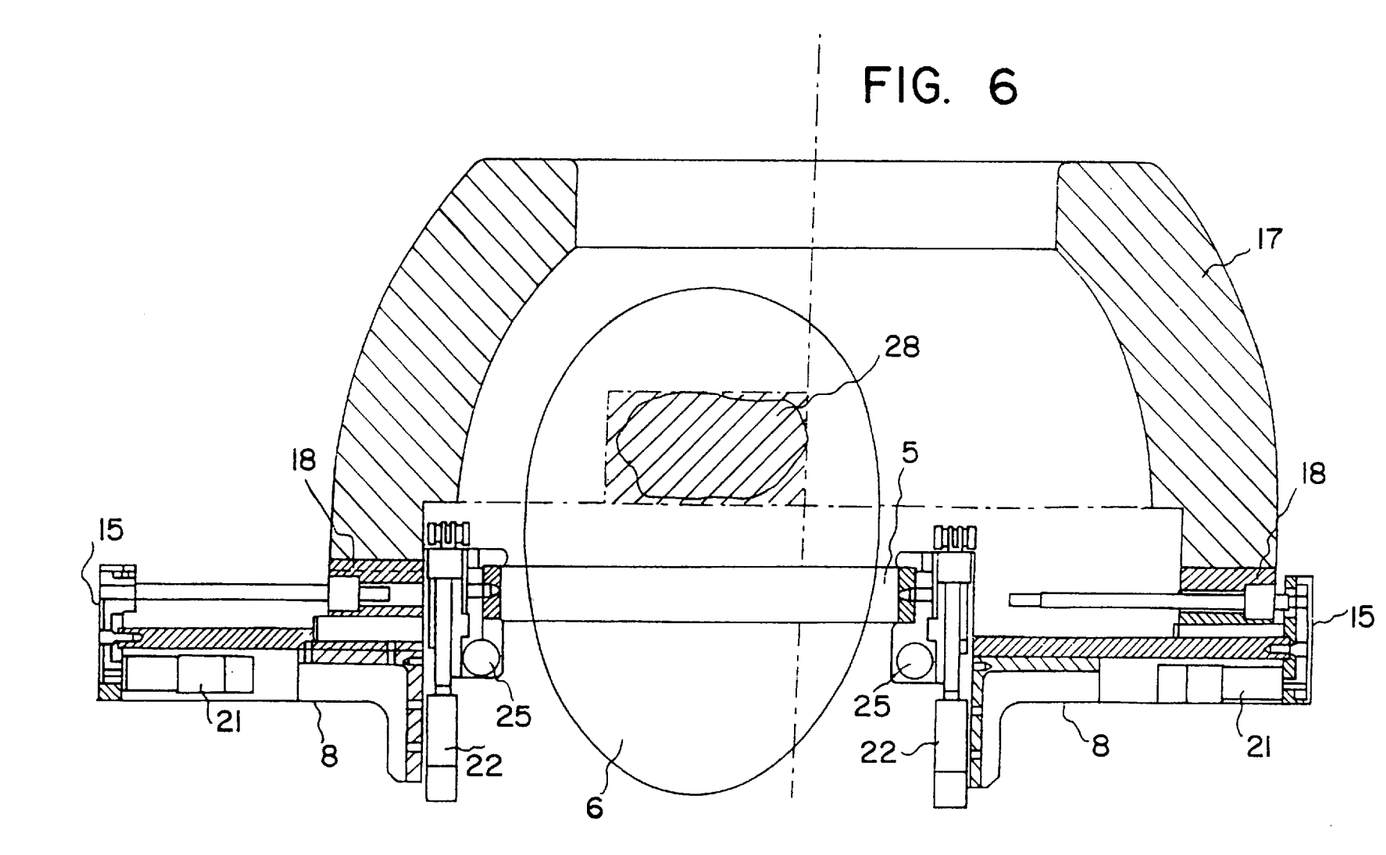
FIG. 6 illustrates a top view of the suspension system illustrated in FIG. 5.

FIG. 6 more completely illustrates an example of a suspension system which may be used in the practice of the present invention. The outer end of each beam 8 is connected to an associated part of the bracket through a screw jack means 15 which is linked to the electronically controlled cooperating motors 21 within the beam 8. The pair of cooperating motors 21 are preferably operated via control from the computer or the like (not illustrated) following a computer program. Motors 21 function cooperatively and translate the frame device 5 in the X direction. The pair of cooperating motors 21 are opposingly disposed and operate in synchronization. In particular, when the motors do not move the stereotactic frame concurrently the same distance, then the error detection feedback system 170 (not shown) connected to the pair of cooperating motors 21 signals the computer that the orientation of the stereotactic frame is not correct and the program moving the stereotactic frame is stopped so that the stereotactic frame can be reoriented.

The pair of cooperating motors 21 work in conjunction with associated pairs of cooperating motors 22 and 25.

Cooperating motors 21 move the stereotactic frame 5 in the X direction, while cooperating motors 22 move the stereotactic frame 5 in the Y direction, and cooperating motors 25 move the stereotactic frame 5 in the Z direction. The two pairs of cooperating motors 22 and 25 are connected to oppositely disposed beams connected to the stereotactic frame 5 in a similar fashion as the pair of cooperating motors 21 are connected to stereotactic frame 5. The pairs of cooperating motors 22 and 25 also have associated screw jack and gear means similar to those connected to the pair of cooperating motors 21.

While this invention has been particularly described and illustrated with reference to particular embodiments thereof, it will be understood by those of skill in the art that changes in the above description or illustrations may be made with respect to form or detail without departing from the spirit or scope of the invention. In particular, any controlled movement means which allows the object being irradiated to be moved relative to a radiation source may be employed.

We claim:

1. A method of treating a patient with radiation, comprising:

determining the position of a focus point with respect to a radiation unit;

immobilizing a portion of said patient with respect to a frame;

supporting said patient with respect to a base of said radiation unit with said frame;

coupling said frame to a suspension system;

fixing a position of said frame by said suspension system with respect to said radiation unit to determine the position of said patient; and automatically moving said frame by said suspension system with respect to said focus point to expose said patient to radiation from said radiation unit.

2. The method of selectively irradiating an object, as in claim 1, further comprising;

modulating a radiation beam of said radiation unit to modulate a focus volume of said radiation unit.

3. The method of selectively irradiating an object, as in claim 1, further comprising;

modulating a radiation source of said radiation unit to modulate a focus volume of said radiation unit.

4. A radiation appliance, comprising:

a radiation unit for irradiating a patient with a focus volume and a frame coupled to a base of said radiation unit by a suspension system, wherein said frame immobilizes a portion of said patient to be irradiated by said radiation unit, and said suspension system automatically moves said frame to expose said patient to radiation.

5. A radiation appliance, as in claim 4, further comprising:

a computer coupled to said suspension system for controlling said suspension system, said suspension system responds to signals transmitted from said computer by moving said frame to expose said patient to radiation from said radiation unit.

6. A radiation appliance, as in claim 5, wherein:

said computer is coupled to said radiation unit and said computer transmits signals to said radiation unit to modulate at least one radiation beam emitted from said radiation unit.

7. A radiation appliance, as in claim 5, wherein:

said computer is coupled to said radiation unit and said computer transmits signals to said radiation unit to modulate a radiation source of said radiation unit.

\* \* \* \* \*